United States Patent
Wilke et al.

(10) Patent No.: US 8,691,074 B2
(45) Date of Patent: Apr. 8, 2014

(54) METHOD FOR OPERATING A MEASURING DEVICE HAVING AT LEAST ONE PROBE, WHICH HAS AT LEAST ONE ION SELECTIVE ELECTRODE

(75) Inventors: Stefan Wilke, Halle (DE); Anja Harbig, Renningen (DE); Daniel Iten, Wermabwil (CH); Gunter Jahl, Lochgau (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 303 days.

(21) Appl. No.: 13/246,918

(22) Filed: Sep. 28, 2011

(65) Prior Publication Data

US 2012/0073989 A1    Mar. 29, 2012

(30) Foreign Application Priority Data

Sep. 28, 2010    (DE) .......................... 10 2010 041 523

(51) Int. Cl.
   *G01N 27/333*    (2006.01)
(52) U.S. Cl.
   USPC ........... 205/789; 205/788.5; 73/1.03; 73/1.02
(58) Field of Classification Search
   USPC ...................... 204/416–420; 205/789, 789.5; 73/1.01–1.07
   See application file for complete search history.

(56) References Cited

U.S. PATENT DOCUMENTS

2009/0229995 A1*    9/2009  Shalyt et al. ............... 205/778.5

FOREIGN PATENT DOCUMENTS

| DE | 42 26 630 A1 | 10/1993 |
| DE | 10 2008 055 084 A1 | 6/2010 |
| EP | 0 544 237 B2 | 6/1993 |
| EP | 0 588 984 B1 | 3/1994 |
| EP | 0 614 081 B1 | 9/1994 |
| EP | 0 706 647 B1 | 4/1996 |

OTHER PUBLICATIONS

German Search Report.

* cited by examiner

*Primary Examiner* — J. Christopher Ball
(74) *Attorney, Agent, or Firm* — Bacon & Thomas, PLLC

(57) ABSTRACT

A method for operating a measuring device comprising the following steps: providing a first sample of the liquid; ascertaining an updated calibration function by means of a standard addition method, wherein the first sample is supplemented at least once with a standard solution, which has a known concentration of the measured ion; determining a measured value of concentration of the measured ion in the first sample; providing a second sample of the liquid; ascertaining a measured value of concentration of the measured ion in the second sample as a reference measured ion concentration ($c_{ref}$) by means of a reference method; and determining a difference ($c_{disturb}$) between the apparent measured ion concentration ($c_{apparent}$) and the reference measured ion concentration ($c_{ref}$) and deriving a correction value ($c_{korr}$) therefrom for future measured values of concentration of the measured ion in the liquid, as ascertained with the measuring device.

12 Claims, 1 Drawing Sheet

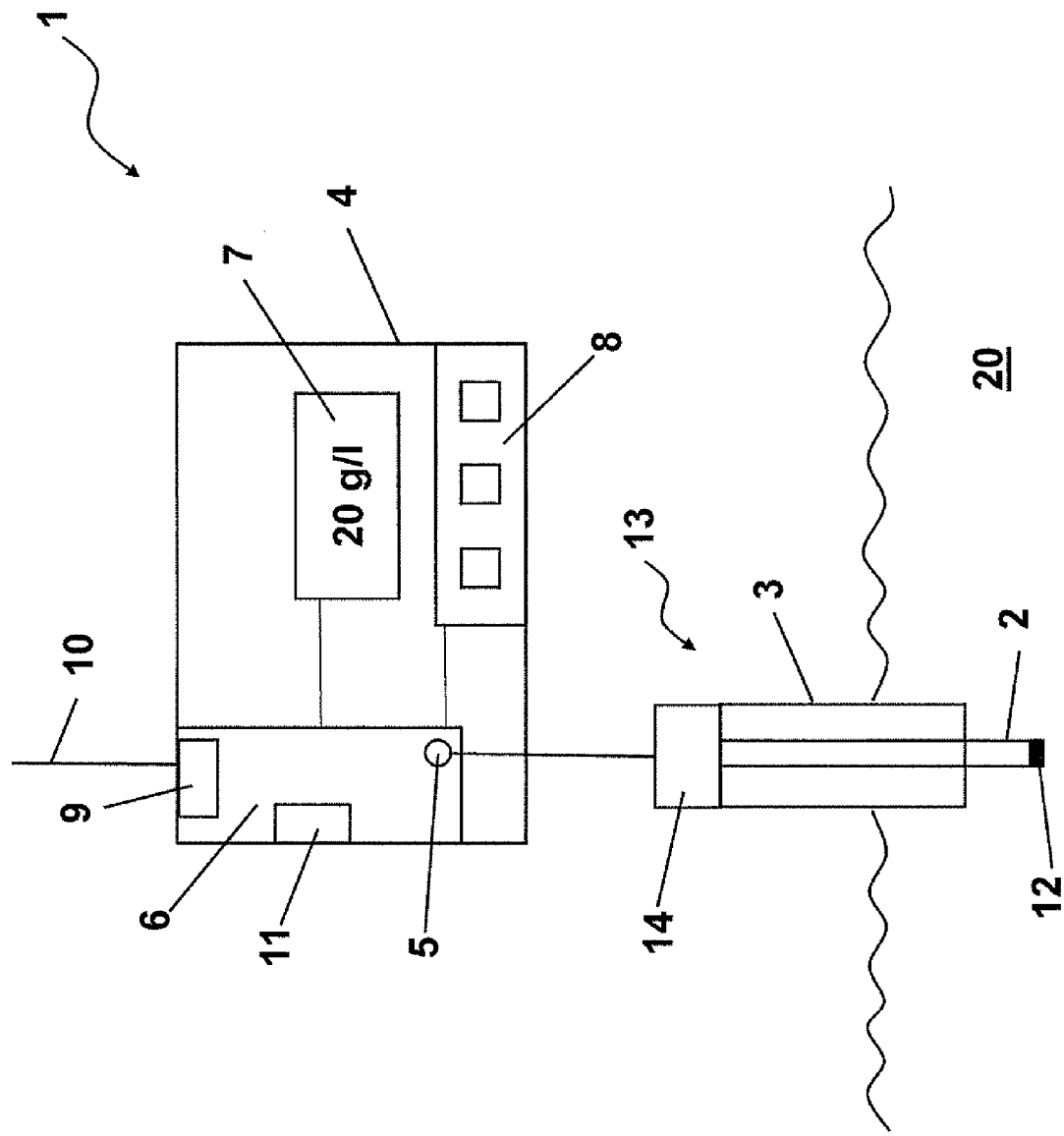

METHOD FOR OPERATING A MEASURING DEVICE HAVING AT LEAST ONE PROBE, WHICH HAS AT LEAST ONE ION SELECTIVE ELECTRODE

TECHNICAL FIELD

The invention relates to a method for operating a measuring device having at least one probe, which has at least one ion selective electrode.

BACKGROUND DISCUSSION

Ion selective electrodes (ISE), in general, are electrochemical sensors, in the case of which the relative change of the equilibrium Galvani voltage between a measured medium and a sensing electrode IS preferably effected by the activity change predominantly of a certain kind of ion. Such ion selective electrodes allow a relatively simple and fast determination of ion concentrations in different media, even e.g. in turbid and colored solutions. Ion selective electrodes are applied, for example, in process liquid analysis and in wastewater analysis.

Potentiometric measurements with ion selective electrodes metrologically correspond largely to the classic pH measurement technique based on pH glass membrane electrodes. Referencing a reference potential of a reference electrode having an essentially constant potential, e.g. the well known Ag/AgCl-electrode, the concentration of a measured ion in a liquid can be determined with high accuracy by means of a high impedance voltmeter with little in the way of apparatus.

Currently, besides glass membranes, membranes known as solid body or polymer membranes are also used as ion selective components of such electrodes. Polymer membranes frequently include a plasticizer as a lipophilic solvent, a salt of the kind of ion to be measured, wherein the salt has a lipophilic counter ion, and a polymer material as a network former for the holding the membrane together. Frequently in the case of cation selective membranes, an ionophore is also present in the membrane. Ion selective electrodes of this type are described, for example, in "Ion selective electrodes," J. Koryta and K. Stulik, Cambridge University Press, 1983, S. 61, or in "Das Arbeiten mit Ionenselektiven Elektroden," K. Cammann, H. Galster, Springer, 1996.

Ion selective electrodes, especially ion selective electrodes based on solid body or polymer membranes, in general, do not respond specifically only to the kind of ion to be measured, also referred to as measured ions in the following, but, instead also to other ions, which are referred to as disturbing ions. Thus it is known, for example, that ammonium ($NH_4^+$) selective electrodes, also referred to in the following as an ammonium-ISE, also respond to the chemically similar potassium ion ($K^+$). In a similar manner a nitrate ion ($NO_3^-$) selective electrode, in the following also referred to as a nitrate-ISE, also responds to chloride ions ($Cl^-$). This is especially disturbing for ISE applications in water analysis, since chloride is present almost universally in drinking water and in wastewater and, above a certain minimum concentration, degrades the measuring of nitrate concentrations.

For example, the selectivity of an ammonium-ISE is, with reference to the molar concentration, 1:10 relative to potassium. The ammonium-ISE thus gives in the presence of a determined ammonium concentration the same measurement signal as in the presence of a ten times as high concentration of potassium. A nitrate-ISE possesses a selectivity of 1:100 relative to chloride with reference to the molar concentration. Thus a 100 times as high concentration chloride is required in order for the nitrate ISE to output the same measurement signal as in the case of a determined nitrate concentration.

In wastewater analysis, the parameters nitrate nitrogen (Nitrate-N), i.e. the mass of nitrogen bound in nitrate ions present in a water sample with reference to the volume of the water sample, and ammonium nitrogen (Ammonium-N), i.e. the mass of nitrogen bound in ammonium ions present in a water sample with reference to the volume of the water sample, play an important role since they are limited by regulations and/or require the paying of fees. Referencing the disturbing influence of a determined mass concentration of chloride ions to the parameter nitrate-N, the selectivity of a nitrate-ISE set forth above is 1:440, for instance. Referencing the disturbing influence of a determined mass concentration of potassium ions to the parameter ammonium-N, the selectivity of an ammonium-ISE is 1:28, for instance.

The parameter ammonium-N in wastewaters of wastewater plants is frequently in a range between 0.1 and 20 mg/l ammonium-N. In municipal wastewater, the potassium concentration typically is in the range of 20 mg/l. In a selectivity of the ammonium-ISE of 1:28 compared to a potassium ion concentration present in the sample, for instance, a measured value of the ammonium-N is obtained, which is around 1 mg/l too high. This is not always acceptable.

There are therefore efforts being made to correct measured values coming from ion selective electrodes and corrupted by the presence of disturbing ions.

An opportunity for compensating cross sensitivities of ion selective electrodes involves measuring the concentration of the disturbing ions, chloride or potassium ions for example, by means of additional electrodes and taking into consideration the selectivity of the particular measuring electrode, thus the ammonium-ISE or the nitrate-ISE for example, in order to correct for the disturbing influence of the measured disturbing ion concentration on the measurement signal of the measuring electrode. An additional selective ISE for the expected disturbing ions is an option for the additional electrode, e.g. an ion selective electrode for chloride ions (chloride-ISE) or an ion selective electrode for potassium ions (potassium-ISE). Such an additional ISE is also referred to as a compensation-ISE of the measuring arrangement.

This solution, however, has disadvantages: The additional ISE must be procured, maintained and, in determined intervals, be renewed by replacing the ion selective membrane. Especially, the additional ISE, like the ISE provided for monitoring the measured ions of real interest, must be calibrated or adjusted at regular intervals. This leads to an additional maintenance effort and also to increased costs in the manufacture of the measuring arrangement.

In such a case, it is to be noted that an incorrectly adjusted compensation-ISE can lead to defective measured values. A measuring device with a measuring ISE and a compensation-ISE consequently has more to it, is more complicated to construct and, finally, more susceptible to disturbances.

Another very simple and frequently sufficient correction method uses the measuring device ISEmax CAS40 available from the present assignee for measuring and monitoring ammonium concentration using an ammonium ISE in municipal wastewater treatment plants. In such a case, the fact is utilized that the concentration of the potassium ions, which act as disturbing ions for the ammonium-ISE, fluctuates in the water of municipal wastewater treatment plants in general only a little. Therewith the disturbing influence of the potassium ions is essentially constant and can therefore be compensated by lessening the measured value obtained from the ammonium-ISE by a fixed, predetermined amount. In the case of an average concentration of potassium ions of 20 mg/l, for example, an inflated reading of about 1 mg/l ammonium-N is caused. This value can, for example, be fixedly predetermined as a correction value and subtracted from each concentration value derived from the measurement signal delivered from the ammonium ISE to form a corrected measured value. To the extent that fluctuations of the potassium ion concentration occur in a relatively narrow range of about 15 mg/l and 25 mg/l, for example, in the liquid to be monitored, there results only a relatively small error, which can be accepted in many applications. Ideally, the correction value is set by a skilled technician who can rely on experiences with the disturbing ion concentrations present at the actual measuring point and their influence on the accuracy of measurement of the measuring device.

SUMMARY OF THE INVENTION

An object of the invention is to provide an easy method, which is independent of the knowledge of a skilled technician, for operating a measuring device having an ion selective electrode measuring concentration of a measured ion in a liquid, wherein cross sensitivities of the ion selective electrode are compensated.

This object is achieved by a method for operating a measuring device having at least one probe, which has at least one ion selective electrode, and which is embodied to output a measurement signal dependent on concentration of a measured ion in a liquid, wherein the measuring device is embodied to represent a measured value of concentration of the measured ion from the measurement signal output by the probe, based on a calibration function, wherein the method includes the following steps:

providing a first sample of the liquid;
ascertaining an updated calibration function by means of a standard addition method, wherein the first sample is supplemented at least once with a standard solution, which has a known concentration of the measured ion;
determining a measured value of concentration of the measured ion in the first sample as an apparent measured ion concentration based on the updated calibration function;
providing a second sample of the liquid, wherein the composition of the second sample corresponds to the composition of the first sample;
ascertaining a measured value of concentration of the measured ion in the second sample as a reference measured ion concentration by means of a reference method; and
determining a difference between the apparent measured ion concentration and the reference measured ion concentration and deriving a correction value therefrom for future measured values of concentration of the measured ion in the liquid, as ascertained by the measuring device.

The correction value so obtained is no longer purely dependent on the experience of a service person, but instead is obtained based on a reference measurement. Therewith, the compensation of disturbance effects and cross sensitivities of the ion selective electrode can also be performed by untrained personnel. Additional measuring probes for determining the concentration of disturbing ions are not required with this method. The reference method ideally makes a very exact measured value of the actual measured ion concentration available. While previous compensation methods are based on either simultaneously measuring or estimating the concentration of the disturbing ions and deriving a correction value therefrom, the concentration of the measured ions is ascertained by means of the reference method so that through the correction value all disturbing influences in addition to the disturbing ion concentration, for example, other compounds present in the to be monitored liquid, are taken into consideration. This is especially advantageous in the case of applications in unknown or atypical wastewaters.

In the standard addition method, a determined amount of a standard solution with a known concentration is added to the first sample one or a number of times, here also referred to as "supplementing the sample." Preferably, after each supplementing of the first sample with the standard solution, a measurement signal of the probe representing the concentration of the measured ion in the supplemented first sample is registered. If there are a sufficient number of calibration measurement points from the supplementings of the sample, the concentration of the measured ion in the original sample can be calculated, for example, by means of linear regression. Besides the updated calibration function based on the calibration measurement points obtained through the measurements of the supplemented sample, moreover, especially the zero-point or axial intercept and, in given cases, the slope of a calibration line, can be ascertained.

The measured ion concentration present in the sample before supplementing can be ascertained from the calibration function through extrapolation.

Ascertaining an updated calibration function by means of the standard addition method can at least comprise steps as follows:

Supplementing the first sample with a first predetermined amount of the standard solution;
registering a probe measurement signal that represents concentration of the measured ion in the supplemented first sample;
optionally supplementing the first sample one or more times anew with an additional predetermined amount of the standard solution and registering a probe measurement signal representing concentration of the measured ion in each newly supplemented first sample; and
determining at least one parameter of a predetermined calibration function, especially determining at least the zero point of a calibration line.

For example, a line, a logarithmic function, a polynomial or some other function can be predetermined as a calibration function for describing the relationship of the measurement signal of the ion selective electrode to concentration of the measured ion in the liquid to be monitored. The standard addition method serves to ascertain, by regression, parameters of the predetermined calibration function, e.g. zero point, axial intercept or coefficients. Frequently a calibration line serves as a calibration function in the case of ion selective electrodes. Through linear regression, the zero-point and, in given cases with the presence of a sufficient number of measurement points also the slope of the calibration line is then ascertained from the measurement points ascertained through the standard addition method.

The reference method can be a photometric or spectroscopic method, or a chemical analytical method, especially a titrimetric or a gravimetric determination.

The measuring device can serve to monitor a liquid collected in a process vessel, especially a pipe or a vat. In this case, an amount of liquid can be removed from the process vessel for providing the first sample and the second sample. In this way, it is assured that the composition of the second sample corresponds to the composition of the first sample. Of course, the first and the second sample can also be removed from the process vessel one after the other, i.e. at different points in time, as long as the composition of the second sample corresponds to the composition of the first sample. A "corresponding composition" here means that the samples have essentially the same concentration of disturbing ions and ions to be measured as well as a uniform water matrix, i.e. a uniform percentage of other components present in the wastewater.

The correction value can be set to equal the difference between the apparent measured ion concentration and the reference measured ion concentration. This correction value is then subtracted from each measured value ascertained from a probe measurement signal based on the updated calibration function, to compensate for the disturbing influences.

Alternatively, a correction value, which is smaller than the difference between the apparent measured ion concentration and the reference measured ion concentration, can be predetermined. This smaller correction value is then correspondingly subtracted from each measured value, which is ascertained from a probe measurement signal based on the updated calibration function, to compensate for the disturbing influences. This is advantageous when concentration of the measured ions, e.g. ammonium or nitrate, in the liquid to be monitored is very small and concentration of disturbing ions relative to concentration of the measured ions fluctuates significantly. In this case, negative measurement results can result from the subtraction of the ascertained difference from the apparent measured ion concentration and the reference measured ion concentration from the measured values ascertained from the measurement signals of the probe. In this case, it is advantageous to provide the opportunity for a service person to provide a somewhat lower correction value than the complete difference between the apparent measured ion concentration and the reference measured ion concentration. In this way, it is true, the disturbing influences are only corrected in part; on the other hand, however, negative measurement results are prevented.

The measuring device can comprise a control unit with a data processing system, a display unit, especially to display the data processed in the control unit, and an input unit to input commands to the control unit. The step of updating the calibration function can then be performed by the data processing system based on a computer program stored in a memory of the data processing system, wherein the updated calibration function or updated parameter of the calibration function is stored in a memory of the data processing system in order to have such available for ascertaining future measured values with the measuring device. The control unit with the data processing unit can be arranged in a single module, for example, in a single measurement transmitter housing. It is, however, equally possible to distribute the functions of the control unit to a number of devices connected with one another for the exchange of data, for example, a first measurement transmitter unit accommodated in a measurement transmitter housing and, connected with this, a superordinated unit, for example, a computer or a process control station connected with the measurement transmitter via a network. Also, a part of the functions of the control unit can be performed in a microcomputer arranged in the probe and connected to a remote measurement transmitter unit for data exchange.

The difference between the apparent measured ion concentration and the reference measured ion concentration can also be ascertained by the data processing system by means of an additional computer program stored in a memory of the data processing system and be output to the display unit. A service person can then decide whether the difference between the apparent measured ion concentration and the reference measured ion concentration should be used as a correction value. This option can be selected by the service person through an input via an input system of the control unit. Alternatively, the service person can also derive a correction value differing from the output for the difference between the apparent measured ion concentration and the reference measured ion concentration. For example, the derived correction value selected can be smaller than the difference that was output. The correction value derived from the difference that was output can be input by the service person via the input system of the control unit.

The correction value can be stored in a memory of the data processing unit. There, it is available to the data processing unit, especially a microprocessor of the data processing unit, for ascertaining future measured values of the ion concentration from the apparent measured values of the ion concentration ascertained using the calibration function.

If the measuring device is to be applied for monitoring a liquid, for example, the effluent of a municipal water treatment plant, the method for operating the measuring device can furthermore comprise steps as follows:
  Registering, by means of the probe, at least one measurement signal, which represents a measured ion concentration in a liquid contained in a process vessel;
  deriving an apparent measured value of the measured ion concentration from the measurement signal by means of the updated calibration function; and
  deriving a corrected measured value of the measured ion concentration from the apparent measured value of the measured ion concentration by subtracting the correction value from the apparent measured value of the measured ion concentration.

BRIEF DESCRIPTION OF THE DRAWINGS

The invention will now be explained in greater detail based on the illustrated example of an embodiment shown in the drawing, the sole FIGURE of which shows as follows:

FIG. 1 is a measuring device having a probe comprising an ion selective electrode.

DETAILED DISCUSSION IN CONJUNCTION WITH THE DRAWING

The measuring device 1 schematically shown in FIG. 1 includes a probe 13, which has a electrode 2 with an ion selective membrane 12 selective for certain measured ions, for example, ammonium ions or nitrate ions. A potential, which is dependent on concentration of the measured ions in the liquid 20, arises on the ion selective membrane 12 in contact with a liquid 20 to be monitored. In a potentiometric measuring method, the potential arising on the membrane 12 is measured relative to the potential of the reference electrode 3. The reference electrode 3 can be an Ag/AgCl electrode, for example. In the present example, the ion selective electrode 2 and the reference electrode 3 form a single rod measuring chain 13, which is connected via an interface 14 to a measurement transmitter 4 serving as a control unit of the measuring device 1. The measurement signal of the probe 13 is the measuring chain voltage of the single rod measuring chain. For example, the measurement signal is converted at a probe interface 14 embodied as a sensor plug head and is transmitted to the measurement transmitter 4. The measurement signal can be conditioned and transmitted via the interface 14 as an analog signal. However, it is also possible that the interface 14 has an analog/digital converter, which digitizes the measuring chain voltage and feeds it to a microcontroller for additional processing; the microcontroller can likewise be provided as a component of the interface 14. The transmission from the interface 14 to the measurement transmitter 4 can be by wire or wireless, e.g. via an inductive, capacitive or optical coupling or even via radio.

The measurement transmitter 4 has an input 5, via which the measurement signal of the probe 13 is input into a data processing system 6 of the measurement transmitter 4. The data processing system 6 comprises especially a processor, e.g. a microcontroller, and a data memory, e.g. an EEPROM data memory, in which data and programs can be stored. In addition to the data processing system 6, the measurement transmitter 4 has a display system 7, by means of which, for example, measured values, operating data, commands input by a user, a selection menu, and warning reports can be displayed. In such case, it can be, for example, a conventional display. Moreover, the measurement transmitter 4 has an input system 8, via which a user can input commands, for example, by selection from a plurality of menu points indicated on the display system. The input system 8 can comprise a keyboard, one or a number of switches, especially a rotating push button switch, a touch sensitive surface or other known input means.

The measurement transmitter 4, moreover, can include another interface 9 with a data line 10 for forwarding data from the data processing system 6 to a superordinated unit, especially a process control station, via a network, for example, a bus system or a network, e.g. Ethernet. The measurement transmitter 4 can have a further interface 11, for example, a USB interface, for connecting an external memory, especially a transportable memory.

A measurement program executable by the processor of the data processing system 6 is stored in a memory of the data processing system 6; the measurement programs serves to ascertain measured values based on the measuring signals of the probe 3 obtained over the interface 5. For this, a calibration function is stored in an additional memory of the data processing system 6; the calibration function represents the measured ion concentration as a function of the measurement signal of the probe 3. In the example described here, a line is stored as calibration function; the calibration line represents the measuring chain voltage of the probe 3 as a function of the base 10 logarithm of the measured ion concentration, i.e. E(log(c)). By means of the calibration line, each value of the measuring chain voltage is associated with a determined measured ion concentration or a measured ion activity, which is converted to a measured ion concentration. In the measurement operation of the measuring device 1, the processor executing the measurement program accesses the memory, in which the calibration line is stored in order to ascertain, based on the calibration line, a measured ion concentration for each registered measurement signal of the probe 3.

The ion concentration measurement so ascertained is, however, only an apparent measured ion concentration $c_{apparent}$ of the liquid 20, since it, as previously described, is influenced by disturbing influences, e.g. disturbing ions present in the liquid 20. Therefore a correction value $c_{korr}$ is stored in a data memory of the data processing installation. The processor executing the measurement program accesses this storage for ascertaining a corrected measured ion concentration. The correction value $c_{korr}$ stored there is subtracted from the ascertained apparent measured ion concentration $c_{apparent}$. The corrected measured ion concentration so ascertained is then output to the display unit 7 and/or forwarded to the superordinated unit via the interface 9 and/or stored in a memory of the measurement transmitter 4.

The calibration function can be updated from time to time. In the example described here the calibration function is a line. To update in this case, the zero point or the axial intercept of the calibration line. If a sufficient number of calibration measurement points are present, also the slope of the calibration line is updated. This procedure is also referred to as adjusting or calibrating. The correction value $c_{korr}$ can also be newly ascertained from time to time, preferably simultaneously with the adjusting or calibrating.

Ascertaining a correction value $c_{korr}$ is described in greater detail as follows:

In a first step, a determined amount of liquid is removed from the liquid 20 to be monitored; the liquid 20 can be, for example, water from the effluent of a municipal wastewater plant. The amount of liquid taken is divided into two samples. Alternatively, of course, the two samples can also be removed one after the other, especially with some time between samplings, as long as it is certain that the two samples correspond to one another in their composition.

The first sample serves for updating the calibration function stored in the memory of the data processing system 6. This update is performed with the assistance of a standard addition method.

In a first step for this, the probe 3 is immersed into the sample; the measurement signal of the probe 3 is registered by the measurement transmitter 4 and stored as a first calibration measurement point. Thereafter, a predetermined amount of a standard liquid with a known concentration of the measured ion, e.g. with a known ammonium ion concentration or nitrate ion concentration, is added to the sample. This method step is also referred to as "supplementing." The probe is again immersed in the solution so supplemented and the measurement signal of the probe 3 of the measurement transmitter 4 is registered and stored as a second calibration measurement point. The sample is supplemented at least once, preferably multiple times and, in each case, a further calibration measurement point is registered and stored in the measurement transmitter 4.

Depending on how many calibration measurement points are present, a 1 point calibration can be performed to determine the zero point of the calibration line; a 2 point calibration can be performed to determine the zero point and slope of the calibration line; or, in the case of presence a larger amount of calibration measurement points, a regression method can be performed to determine the calibration line. A program module is stored for this purpose in the memory of the data processing system 6. The program module is performable by the processor of the data processing system 6, in order to ascertain an updated function or updated parameter from the stored calibration measurement points and to store this in a memory, which the processor accesses each time anew, when running the measurement program to determine values of measured ion concentration.

From the calibration line so ascertained or updated, a value for the measured ion concentration in the original, not supplemented, first sample can be ascertained. The measured concentration value so ascertained gives an apparent measured ion concentration, which is composed of the sum of the measured ion concentration $c_{meas}$ actually present and the totality of the disturbing influences $c_{disturb}$ according to the relationship:

$$c_{apparent} = c_{meas} + c_{disturb}$$

If the probe 3 has an ammonium ISE, a potassium ion concentration present in the sample is essentially added to the totality of the disturbing influences $c_{disturb}$. If the probe is a nitrate ISE, a chloride ion concentration present in the sample is essentially added to the totality of the disturbing influences $c_{disturb}$.

In the second sample, the measured ion concentration is ascertained by means of a reference method. The reference method can be, for example, a photometric laboratory method, e.g. one known as a "cuvette test," but also another method of analytical chemistry, e.g. a titrimetric or gravimetric method. Preferably, the reference method should have a higher selectivity for the measured ion than the ion selective electrode 2. Especially, it should not be influenced by the disturbing influences $c_{disturb}$, which influence the potential of the ion selective electrode 2, or be influenced to a lesser degree than the ion selective electrode 2. The reference measured ion concentration $c_{ref}$ ascertained in the reference method is thus a more exact measured value of the actual measured ion concentration $c_{meas}$ in the sample. The reference measured ion concentration $c_{ref}$ can therefore be set approximately equal to the actual measured ion concentration $c_{meas}$. The disturbing influence $c_{disturb}$ of other ions contained in the sample is therefore calculated from $c_{apparent}$ according to the relationship:

$$c_{disturb} = c_{apparent} - c_{ref}$$

The correction value $c_{korr}$ mentioned further above is derived from $c_{disturb}$ and is stored in a data memory of the measurement transmitter 4. All measured values ascertained from measurement signals of the probe by means of the calibration function 3 are, as described above, lessened by this correction value, in order to obtain a corrected measured ion concentration that better corresponds to the actual measured ion concentration $c_{meas}$.

The correction value $c_{korr}$ can be set, for example, equal to the ascertained disturbing influence $c_{disturb}$. This can be automatically performed by the data processing system 6 of the measurement transmitter 4 by means of a corresponding program module stored in the memory.

If the measured ion concentration, e.g. the ammonium ion concentration, in a measuring of a liquid to be monitored is very small and the disturbing ion concentration in the liquid 20 to be monitored strongly fluctuates at a point in time when the influence of disturbing ions is smaller than at the point in time of the determination of the disturbance ion influence $c_{disturb}$, can happen that the apparent measured ion concentration $c_{apparent}$ is smaller than the ascertained correction value $c_{korr}$. Correspondingly, a negative measured value results in this case by subtracting the correction value $c_{korr}$ from the apparent measured ion concentration $c_{apparent}$. In order to prevent such results, $c_{korr}$ can be set smaller than $c_{disturb}$ ($0 < c_{korr} < c_{disturb}$), which only corresponds to a partial correction.

For this, an opportunity for input can be provided in the program for ascertaining the correction value $c_{korr}$ stored in the memory of the data processing system 6 and executable by the processor of the data processing system 6 in order to have $c_{korr}$ be set as an input by a service person by means of the input apparatus 8. In this case, the value $c_{disturb}$ ascertained in the data processing unit 6 and representing the totality of the disturbing influences can be output via the display unit 7 so that a service person can derive and input a somewhat smaller correction value $c_{korr}$ based on the value of $c_{disturb}$, for example. Alternatively, it is also possible to provide a program in a memory of the data processing system 6 for carrying out an algorithm, by means of which a correction value $c_{korr}$ representing the totality of the disturbing influences first ascertained is derivable from a value $c_{disturb}$ based on experiential values or a model of the disturbing influences on the ion selective electrode 2. This program can be executed by the processor of the data processing system 6, in order to automatically derive a correction value $c_{korr}$ from the value $c_{disturb}$.

The invention claimed is:

1. A method for operating a measuring device having at least one probe, which has at least one ion selective electrode, and which is embodied to output a measurement signal dependent on concentration of a measured ion in a liquid, wherein the measuring device is embodied to represent a measured value of concentration of the measured ion from the measurement signal output by the probe, based on a calibration function; the method comprising the steps of:

providing a first sample of the liquid;
ascertaining an updated calibration function by means of a standard addition method, wherein the first sample is supplemented at least once with a standard solution, which has a known concentration of the measured ion;
determining a measured value of concentration of the measured ion in the first sample as an apparent measured ion concentration based on the updated calibration function;
providing a second sample of the liquid, wherein the composition of the second sample corresponds to the composition of the first sample;
ascertaining a measured value of concentration of the measured ion in the second sample as a reference measured ion concentration by means of a reference method; and
determining a difference between the apparent measured ion concentration and the reference measured ion concentration and deriving a correction value therefrom for future measured values of concentration of the measured ion in the liquid, as ascertained by the measuring device.

2. The method as claimed in claim 1, further comprising the step of:
registering a probe measurement signal representing concentration of the measured ion in the supplemented first sample after each supplementing of the first sample with the standard solution.

3. The method as claimed in claim 1, wherein ascertaining an updated calibration function by means of the standard addition method includes at least the following steps:
supplementing the first sample with a first predetermined amount of the standard solution;
registering a probe measurement signal that represents concentration of the measured ion in the supplemented first sample;
optionally supplementing the first sample one or more times anew with an additional predetermined amount of the standard solution and registering a probe measurement signal representing concentration of the measured ion in each newly supplemented first sample; and
determining at least one parameter of a predetermined calibration function, especially determining at least the zero point of a calibration line.

4. The method as claimed in claim 1, wherein:
said reference method is a photometric or spectroscopic method or a chemical analytical method, which especially comprises a titrimetric or a gravimetric determination.

5. The method as claimed in claim 1, wherein:
the measuring device serves to monitor a liquid collected in a process vessel, especially in a pipe or a vat; and
an amount of liquid is removed from the process vessel to provide the first sample and the second sample, wherein the first sample and the second sample are taken from the removed amount of liquid.

6. The method as claimed in claim 1, wherein:
the correction value is set to equal the difference between the apparent measured ion concentration and the reference measured ion concentration.

7. The method as claimed in claim 1, wherein:
the correction value is set to be smaller than the difference between the apparent measured ion concentration and the reference measured ion concentration.

8. The method as claimed in claim 1, wherein:
the measuring device comprises a control unit having a data processing system, a display unit, especially to display data processed in the control unit, and an input unit to input commands into the control unit; and
said step of updating the calibration function is performed by the data processing system based on a computer program stored in a memory of the data processing system; and
the updated calibration function is stored in a memory of the data processing system, in order to have the updated calibration function available for ascertaining future measured values with the measuring device.

9. The method as claimed in claim 1, wherein:
the difference between the apparent measured ion concentration and the reference measured ion concentration is ascertained by the data processing system based on a computer program stored in a memory of the data processing system and is output via the display unit.

10. The method as claimed in claim 9, wherein:
through an input selected via the input unit, the correction value is set equal to the difference or the correction value is set to a value lower than the difference.

11. The method as claimed in claim 1, wherein:
the correction value is stored in a memory of the data processing unit, in order, in ascertaining future measured values of the ion concentration, to be subtracted from the apparent measured values of the ion concentration ascertained based on the calibration function.

12. The method as claimed in claim 11, further comprising the steps of:
registering, by means of the probe, at least one measurement signal, which represents a measured ion concentration in a liquid contained in a process vessel;
deriving an apparent measured value of the measured ion concentration from the measurement signal by means of the updated calibration function; and
deriving a corrected measured value of the measured ion concentration from the apparent measured value of the measured ion concentration by subtracting the correction value from the apparent measured value of the measured ion concentration.

* * * * *